United States Patent [19]

Hegar et al.

[11] 4,141,890
[45] Feb. 27, 1979

[54] AZO COMPOUNDS HAVING A 3-SULPHOMETHYL-PYRAZOLONE-(5) COUPLER COMPONENT

[75] Inventors: Gert Hegar, Schönenbuch, Switzerland; Gerhard Back, Lörrach, Fed. Rep. of Germany

[73] Assignee: Ciba-Geigy Corporation, Ardsley, N.Y.

[21] Appl. No.: 737,243

[22] Filed: Oct. 29, 1976

Related U.S. Application Data

[63] Continuation of Ser. No. 606,919, Aug. 22, 1975, abandoned, which is a continuation of Ser. No. 396,258, Sep. 11, 1973, abandoned.

[30] Foreign Application Priority Data

Oct. 5, 1972 [CH] Switzerland .................. 14560/72

[51] Int. Cl.$^2$ ............... C09B 29/38; C09B 31/14; C09B 43/12; C09B 62/08
[52] U.S. Cl. ............... 260/153; 260/145 B; 260/147; 260/154; 260/155; 260/156; 260/158; 260/160; 260/161; 260/162; 260/163; 548/358
[58] Field of Search ............... 260/153, 154, 155, 156, 260/158, 159, 160, 161, 162, 163

[56] References Cited

U.S. PATENT DOCUMENTS

| 2,892,831 | 6/1959 | Stephen | 260/153 |
| 3,097,197 | 7/1963 | Tilley et al. | 260/153 |
| 3,109,840 | 11/1963 | Beffa et al. | 260/156 X |
| 3,385,843 | 5/1968 | Remy et al. | 260/163 |
| 3,455,897 | 7/1969 | Knowles | 260/153 |
| 3,655,642 | 4/1972 | Meininger et al. | 260/153 X |

FOREIGN PATENT DOCUMENTS 405,547  7/1966  Switzerland .................. 260/153

Primary Examiner—Charles F. Warren
Attorney, Agent, or Firm—Edward McC. Roberts; Michael W. Glynn

[57] ABSTRACT

Azo compounds of the formula

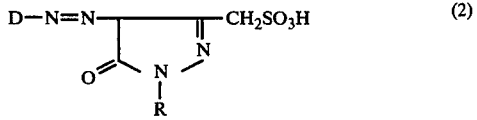

(2)

wherein R is hydrogen, an alkyl or aryl radical and D is the radical of a diazo component are valuable dyestuffs for coloring textile materials.

3 Claims, No Drawings

AZO COMPOUNDS HAVING A 3-SULPHOMETHYL-PYRAZOLONE-(5) COUPLER COMPONENT

This is a continuation of application Ser. No. 606,919, filed on Aug. 22, 1975 which in turn is a continuation of U.S. application Ser. No. 396,258 filed Sept. 11, 1973 (now both abandoned).

The invention relates to azo compounds which contain the radical of a 3-sulphomethyl-pyrazolone-(5), in particular azo compounds of the formula

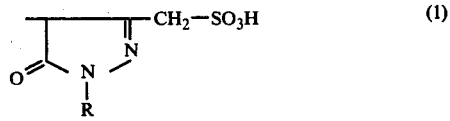 (1)

wherein R represents a hydrogen atom, an alkyl or aryl radical, or a heterocyclic radical. The radical of the formula (1) is bonded through an azo bridge to the radical of a diazo component. The diazo radical is a heterocyclic or aromatic radical which can itself contain an azo group or which is derived from a compound of the anthraquinone, nitroaryl, phthalocyanine, or stilbene series or the like. The diazo radical is in particular a radical of the benzene or naphthalene series.

The azo compounds of the invention can exist in a number of tautomeric forms. In order to simplify the description the compounds in the formulae are illustrated in only one of these tautomeric forms, but it must be expressly emphasised that throughout this specification, especially in the claims, the description always refers to compounds in any of these tautomeric forms.

In particular, the term "pyrazolone" is intended to include also the compounds in question which are substituted in 1-position of the pyrazolone ring by a hydrogen atom as well as the corresponding tautomeric 5-hydroxypyrazoles.

In addition to the sulphomethyl group, the azo compounds according to the invention can be free from water-solubilising groups such as sulphonic acid groups, carboxyl groups, or quaternised amino groups, in particular, however, they can also contain such groups. Above all, the compounds can contain one or more than one reactive radical, for example, a halotriazine radical, in the molecule. In addition to being substituted by water-solubilising groups, the azo compounds can be substituted in the normal way, by still further atoms or groups of atoms, and in particular both in the radical of the diazo component and in the radical R, for example by halogen atoms or hydroxyl, amino, alkyl, aryl, alkoxy, aryloxy, acylamino, cyano, acyl, carbalkoxy, acyloxy or nitro groups, and the like. If the radical of the diazo component contains, in the ortho-position to the azo bridge, a complex-forming group, for example, a hydroxyl, amino or carboxyl group or an alkoxy group, for example, a methoxy group, the compounds in question can optionally be converted into their heavy metal complex compounds either before the introduction of reactive radicals or afterwards.

Possible complex-forming metals are, for example, iron, manganese, nickel, copper, cobalt and chromium. The heavy metal complexes can contain one or two molecules of azo compounds containing the radical of the formula (1), bonded to a metal atom (1:1- or 1:2-complexes). However, in 1:2-complexes one of the two ligand molecules can also be an azo compound which does not possess the radical of the formula (1) as coupling component, that is to say, for example, a compound of the azobenzene type which contains corresponding complex-forming groups.

Groupings capable of reaction with the hydroxyl groups of cellulose or with the amino groups of polyamides to form a covalent chemical bond are possible reactive radicals. Such a grouping is, in particular, a low molecular weight alkanoyl or alkylsulphonyl radical substituted by a removable atom or a removable group, a low molecular weight alkenoyl or alkenesulphonyl radical optionally substituted by a removable atom or a removable group, a carboxylic or heterocyclic radical containing 4-, 5- or 6-rings which is substituted by a removable atom or a removable group and is bonded via a carbonyl or sulphonyl group, or a triazine or pyrimidine radical substituted by a removable atom or a removable group and directly bonded via a carbon atoms, or such a grouping contains such a radical. A six-membered heterocyclic radical with two or three ring nitrogen atoms which contains halogen atoms and is bonded via an —NH— group, in particular a chloro-1,3,5-triazine radical, is preferred as the reactive radical.

The invention relates in particular to compounds of the formula

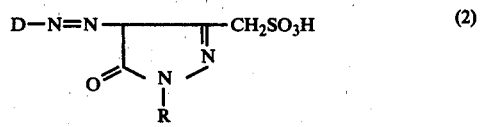 (2)

wherein R is a hydrogen atom, an alkyl radical with at most 4 carbon atoms or an aryl radical, and wherein D is the radical of a diazo component of the benzene or naphthalene series. The invention also relates in particular to compounds which possess reactive radicals, above all cyclic reactive radicals, for example triazine, pyrimidine or cyclobutane radicals, and water-solubilising groups, with reactive radicals can also be contained in the substituent R.

A special group of compounds according to the invention are those of the formula

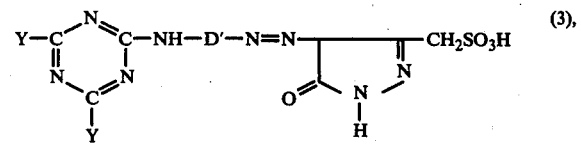 (3), wherein D' is a sulphobenzene radical, one Y is a halogen atom and the other Y is a halogen atom or the radical of an amine to which a fibre-reactive radical may be bonded, of an alcohol, phenol or mercaptan. The benzene radical can also carry further substituents in addition to one or two sulphonic acid groups, as already mentioned.

A further group of interesting compounds is that of the formula

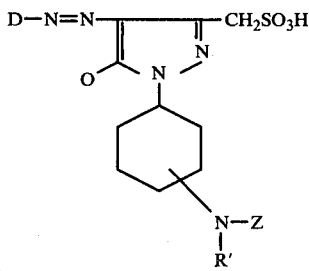

$$(4)$$

wherein D is the radical of a diazo component of the benzene or naphthalene series, in particular a radical which contains water-solubilising substituents, R' is a hydrogen atom or a low molecular alkyl radical, and Z is a reactive radical, in particular a dihalotriazine radical or a monohalotriazine radical which contains the radical of ammonia, an amine, alcohol, phenol or mercaptan, bonded to a carbon atom.

By low molecular alkyl radical are meant in this case alkyl radicals with 1 to 4 carbon atoms, e.g. the methyl, ethyl, propyl, isopropyl, butyl, or β-hydroxyethyl radical.

Importance also attaches to compounds which contain one reactive radical in the diazo and coupling component, for example compounds of the formula (4), which, in addition to the reactive radical Z contain a further reactive radical in the diazo component D.

The manufacture of the azo compounds according to the invention can be carried out by coupling and, where appropriate, metallisation, or by acylation, in order to introduce a reactive radical.

The manufacture by coupling consists in coupling a diazo component, in particular a diazo component of the benzene series, with a 3-sulphomethyl-pyrazolone-(5), in particular of the formula

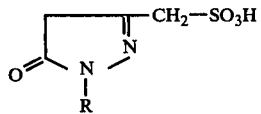

$$(5)$$

wherein R has the meaning indicated in the explanation of the formula (1), and in optionally converting the resulting azo compound into a heavy metal complex by reaction with a heavy metal donor. The starting compounds are preferably diazo components which contain a reactive radical and a water-solubilising group.

The diazotisation is carried out by methods which are in themselves known, for example by means of hydrochloric acid and sodium nitrite. The coupling with the pyridone is also carried out according to methods which are in themselves known, in an acid to weakly alkaline medium.

Depending on the solubility of the components, the reaction with the heavy metal donor is carried out according to conventional methods in various solvents, for example water, ethanol, formamide, glycolethers, pyridine and the like, optionally at elevated temperature, and in a weakly acid to alkaline medium.

As diazo components which can be used for the manufacture of the compounds according to the invention having the radical of the formula (1), or the corresponding heavy metal complexes, the diazo compounds of the following amines may be mentioned: aminobenzene, 1-amino-4-chlorobenzene, 1-amino-4-bromobenzene, 1-amino-4-methyl-benzene, 1-amino-2-nitrobenzene, 1-amino-2,5-dicyanobenzene, 1-amino-4-methylsulphonylbenzene, 1-amino-4-carbalkoxybenzene, 1-amino-2,4-dichlorobenzene, 1-amino-2,4-dibromobenzene, 1-amino-2-methyl-4-chlorobenzene, 1-amino-2-trifluoromethyl-4-chlorobenzene, 1-amino-2-cyano-4-chlorobenzene, 1-amino-2-carbomethoxy-4-chlorobenzene, 1-amino-2-carbomethoxy-4-nitrobenzene, 1-amino-2-chloro-4-cyanobenzene, 1-amino-2-chloro-4-nitrobenzene, 1-amino-2-bromo-4-nitrobenzene, 1-amino-2-chloro-4-carbethoxybenzene, 1-amino-2-chloro-4-methylsulphonylbenzene, 1-amino-2-methylsulphonyl-4-chlorobenzene, 1-amino-2-methylsulphonyl-4-nitrobenzene, 1-amino-4-methylsulphonyl-2-nitrobenzene, 1-amino-2,4-dicyanobenzene, 1-amino-2-cyano-4-methylsulphonylbenzene, 1-amino-2,6-dichloro-4-cyanobenzene, 1-amino-2,6-dichloro-4-nitrobenzene, 1-amino-2,4-dicyano-6-chlorobenzene, 4-aminobenzoic acid cyclohexyl ester, 1-aminobenzene-2-, -3- or-4-sulphonamides, such as the N-methylamide or N,N-dimethylamide or N,N-diethylamide, 2-aminonaphthalene-6-sulphonic acid N,γ-isopropyloxypropylamide, 1-aminobenzene-2-, -3- or -4-sulphonic acid N,γ-isopropyloxypropylamide, 1-aminobenzene-2-, -3- or -4-sulphonic acid N-siopropylamide, 1-aminobenzene-2-, -3- or 4-sulphonic acid N,γ-methoxypropylamide, 1-aminobenzene-2-, -3- or -4-sulphonic acid N,N-bis-(β-hydroxyethyl)amide, 1-amino-4-chlorobenzene-2-sulphonamide and the N-substituted derivatives, 2-aminothiazole, 2-amino-5-methylsulphonyl-thiazole, 3-amino-5-chloro-benzisothiazole, 2-amino-4-methylthiazole, 2-amino-4-phenylthiazole, 2-amino-4-(4'-chloro)-phenylthiazole, 3-aminopyridine, 3-aminoquinoline, 3-aminopyrazole, 3-amino-1-phenyl-pyrazole, 3-aminoindazole, 3-amino-1,2,4-triazole, 5-(methyl-, ethyl-, phenyl- or benzyl)-1,2,4-triazole, 3-amino-1-(4'-methoxyphenyl)pyrazole, 2-aminobenzthiazole, 2-amino-6-methylbenzthiazole, 2-amino-6-methoxybenzthiazole, 2-amino-6-chlorobenzthiazole, 2-amino-1,3,4-thiadiazole, 2-amino-1,3,5-thiadiazole, 2-amino-4-phenyl- or-4-methyl-1,3,5-thiadiazole, 4-aminoazobenzene, 3,2'-dimethyl-4-aminoazobenzene, 2-methyl-5-methoxy-4-aminoazobenzene, 4-amino-2-nitroazobenzene, 2,5-dimethoxy-4-aminoazobenzene, 4'-methoxy-4-aminoazobenzene, 2-methyl-4'-methoxy-4-aminoazobenzene, 3.6.4'-trimethoxy-4-aminoazobenzene, 4'-chloro-4-aminoazobenzene, 2'- or 3'-chloro-4-aminoazobenzene, 3-nitro-4-amino-2',4'-dichloroazobenzene, 4-aminoazobenzene-4'-sulphonic acid amide, 1- or 2-aminonaphthalene, 4-methoxy-5-chloro-2-aminophenyl, 6-acetylamino-4-chloro-2-aminophenol, 6-nitro-4-chloro-2-aminophenol, 6-nitro-4-methyl-2-aminophenol, 3-amino-4-hydroxyacetophenone, 6-nitro-4-acetylamino-2-aminophenol, 5-nitro-3-amino-4-hydroxy-acetophenone, 2-aminophenol-4-carboxylic acid amide, 4,6-dichloro-2-aminophenol, 3,4,6-trichloro-2-aminophenol, 4-nitro-6-chloro-2-aminophenol, 6-nitro- or 6-chloro-2-aminophenol-4-sulphonic acid amide, 4-nitro-2-aminophenol-5- or -6-sulphonic acid amide, 2-aminophenol-5-methylsulphone, 2-aminophenol, 4- or 5-aminophenol, 4- or 5-chloro-2-aminophenol, 4,5-dichloro-2-aminophenol, 4-chloro-5-nitro-2-aminophenol, 2-aminophenol-4- or -5-sulphonic acid, 3,4,6-trichloroaminophenol, 4-chloro-2-aminophenol-6-sulphonic acid, 6-chloro-2-aminophenol-4-sulphonic acid, 4-nitro-2-aminophenol-6-sulphonic acid, 6-nitro-2-aminophenol-4-sulphonic acid, 2-aminophenol-4,6- disulphonic acid, 4,6-dinitro-2-aminophenol, 6-acetylamino-2-aminophenol-4-sulphonic acid, 4-acetylamino-2-aminophenol-6-sulphonic acid, 4-methyl-2-aminophenol, 4-methoxy-2-aminophenol, 2-aminophenol-4-sulphonamide, 2-aminophenol-4-sulphon-N-β-hydroxyethylamide, 2-aminophenol-4-sulphon-N-methylamide, 2-aminophenol-5-sulphonamide, 4-chloro-2-aminophenol-5- or -6-sulphonamide, 2-aminophenol-4-sulphon-N,N-dimethylamide, 2-aminophenol-4-methylsulphone, 2-aminophenol-4-ethylsulphone, 6-acetylamino-4-nitro-2-aminophenol, 2-aminophenol-4,β-hydroxyethylsulphone, anthranilic acid, 2-amino-3-naphthoic acid, 4- or 5-chloroanthranilic acid, 4- or 5-nitroanthranilic acid, 4- or 5-acetylaminoanthranilic acid, 4- or 5-sulphoanthranilic acid, anthranilic acid 4-sulphonamide, anthranilic acid 4- or 5,β-hydroxyethylsulphone, anthranilic acid 4- or 5-ethylsulphone, 4-chloro-2-aminophenol-5-sulphonic acid N-methylamide, 4- or 5-benzoylaminoanthranilic acid, 2-anisidine, 4- or 5-chloro-2-anisidine, 4- or 5-nitro-2-anisidine, 2-anisidine-4- or -5-sulphonic acid, 2-methoxy-5-methylaniline, 2,5-dimethoxyaniline, 2-anisidine-4- or -5-β-hydroxyethylsulphone, 2-amino-1-naphthol-4,8-disulphonic acid, 1-amino-2-naphthol-4-sulphonic acid, 1-amino-2-naphthol-4-sulphonamide, 6-nitro-1-amino-2-naphthol-4-sulphonic acid, 6-acetylamino-1-amino-2-naphthol-4-sulphonic acid, 4-(2',5'-disulphophenylazo)-2-methoxy-5-methylaniline, 4-(2',5'-disulphophenylazo)-2,5-dimethoxyaniline, 4-(2',5'-disulphophenylazo)-2-methoxy-1-naphthylamino-6-sulphonic acid, 4-(1',5'-disulphonaphth-2'-ylazo)-2,5-dimethoxyaniline, 4-(2',3'- or 4'-sulphophenylazo)-2-methoxyaniline, dianisidine, benzidine-3,3'-dicarboxylic acid, 4-(2'-, 3'- or 4'-sulphophenylazo)-2-methoxy-5-methylaniline, 4-(2'-, 3'- or 4'-sulphophenylazo)-2,5-dimethoxyaniline, 4-(2',5'- or 3',5'-disulphophenylazo)-2-methoxyaniline, 4-(3',5'-disulphophenylazo)-2-methoxy-5-methylaniline, 4-(3',5'-disulphophenylazo)-2,5-dimethoxyaniline, 4-(2'-carboxy-4'- or -5'-sulphophenylazo)-2-methoxyaniline, 4-(2'-carboxy-4- or -5'-sulphophenylazo)-2,5-dimethoxyaniline, 4-(2'-carboxy-4'- or -5'-sulphophenylazo)-2-methoxy-5-methyl-aniline, 4-(6',8'-disulphonaphth-2'-ylazo)-2-methoxyaniline, 4-(6',8'-disulphonaphth-2'-ylazo)-2-methoxyaniline, 4-(6',8'-disulphonaphth-2'-ylazo)-2-methoxy-5-methoxy-aniline, 4-(6',8'-disulphonaphth-2'-ylazo)-2,5-dimethoxyaniline, 4-phenylazo-2-aminophenol, methanilic acid, sulphanilic acid, orthanilic acid, 1-amino-4-methylbenzene-2-sulphonic acid aniline-2,5-disulphonic acid, 2-naphthylamine-1-sulphonic acid, 2-naphthylamine-1,5-disulphonic acid, 2-naphthylamine-4,8-disulphonic acid, 2-naphthylamine-4,6,8- or 3,6,8-trisulphonic acid, 1-amino-4-(β-sulphatoethylsulphonyl)-benzene, 1-amino-3-(β-sulphatoethyl-sulphonyl)benzene, 1-amino-2-methoxy-4-(β-sulphatoethylsulphonyl)-5-methyl-benzene, 1-amino-4-(β-sulphatoethylsulphonamido)benzene, 1-amino-4-(β-hydroxyethylsulphonyl)-benzene, 1-amino-4-(β-sulphoethylsulphonylmethylamido)-benzene.

As coupling components there may be cited: 3-sulphomethyl-pyrazolone-(5), 1-methyl-3-sulphomethyl-pyrazolone-(5), 1-ethyl-3-sulphomethyl-pyrazolone-(5), 1-propyl-3-sulphomethyl-pyrazolone-(5), 1-phenyl-3-sulphomethylpyrazolone-(5), 1-(2'-chlorophenyl)-3-sulphomethyl-pyrazolone-(5), 1-(2'-sulphophenyl)-3-sulphomethyl-pyrazolone-(5), 1-(3'-sulphophenyl)-3-sulphomethyl-pyrazolone-(5), 1-(4'-sulphophenyl)-3-sulphomethyl-pyrazolone-(5), 1-(4'-nitrophenyl)-3-sulphomethyl-pyrazolone-(5), 1-(2'-methylphenyl)-3-sulphomethyl-pyrazolone-(5), 1-(4'-methylphenyl)-3-sulphomethyl-pyrazolone-(5), 1-(4'-methoxyphenyl)-3-sulphomethyl-pyrazolone-(5), 1-(2',5'-dimethylphenyl)-3-sulphomethyl-pyrazolone-(5), 1-benzyl-3-sulphomethyl-pyrazolone-(5), 1-cyclohexyl-3-sulphomethyl-pyrazolone-(5), 1-(4'-fluorophenyl)-3-sulphomethyl-pyrazolone-(5), 1-(2'-chloro-5'-sulphophenyl)-3-sulphomethyl-pyrazolone-(5), 1-(4',8'-disulphonaphth-2'-yl)-3-sulphomethyl-pyrazolone-(5), 1-(2',5'-dichlorophenyl)-3-sulphomethyl-pyrazolone-(5), 1-(4'-acetaminophenyl)-3-sulphomethyl-pyrazolone-(5), 1-(4'-bromophenyl)-3-sulphomethyl-pyrazolone-(5), 1-(4'-chlorophenyl)-3-sulphomethylpyrazolone-(5), 1-(2'-cyanoethyl)-3-sulphomethyl-pyrazolone-(5), 1-(2'-methoxyethyl)-3-sulphomethyl-pyrazolone-(5), 1-(3'- or 4'-aminophenyl)-3-sulphomethylpyrazolone-(5), 1-(4'-amino-2'-sulphophenyl)-3-sulphomethylpyrazolone-(5), 1-(2'-chloro-6'-methyl-4'-sulphophenyl)-3-sulphomethylpyrazolone-(5), 1-(2'-hydroxyethyl)-3-sulphomethyl-pyrazolone-(5), 1-(2'-methoxyphenyl)-3-sulphomethyl-pyrazolone-(5), 1-(3'-acetaminophenyl)-3-sulphomethyl-pyrazolone-(5).

The coupling components are manufactured by reacting a haloacetoacetic ester, e.g. a chloroacetoacetic ester, with a sulphite, e.g. sodium sulphite, and condensing the resulting sulphoacetoacetic ester with hydrazine, when the desired 3-sulphomethyl-pyrazolone-(5) is formed accompanied by the splitting off of water. The reaction and condensation take place in aqueous, acid or alkaline solution at normal or elevated temperature.

Azo compounds with the radical of formula (1), or the corresponding heavy metal complexes, which contain one or more reactive groups, can be manufactured by using diazo or coupling components which already contain reactive groups. However, in many cases it is possible to introduce reactive groups subsequently into the azo compounds. The introduction can be effected after the coupling or metallisation. Particular interest attaches to these compounds with the radical of the formula (1) which contains a six-membered heterocyclic reactive radical bound via an amino group.

The introduction of the reactive radical is preferably effected by acylating corresponding aminoazo compounds or coupling components which contain an acylatable amino group, or corresponding diazo components, which, in addition to the amino group to be diazotised, still contain a further acylatable amino group, or a group which can be converted to an acylatable amino group, for example by reduction or saponification, such for example the nitro group or the acetylamino group.

Corresponding diazo components which, as described above, are suitable for introducing a reactive radical, are, for example: 1,3-diaminobenzene-4-sulphonic acid, 1,4-diaminobenzene-2-sulphonic acid, 1,4-diaminobenzene-2,5- or -2,6-disulphonic acid, 1-amino-4-nitrobenzene, 1-amino-2-chloro-4-nitrobenzene, 6-acetylamino-4-chloro-2-aminophenol, 6-nitro-4-methyl-2-aminophenol, 4-nitro-2-aminophenol-6-sulphonic acid, 6-acetylamino-1-amino-2-naphthol-4-sulphonic acid and other compounds, for example compounds mentioned in the list of possible diazo components.

Examples of suitable aminoazo compounds into which the reactive radicals can be introduced after the coupling are the coupling products of the diazo components cited hereinabove with pyrazolones of the formula (5).

The compounds of the formula (4) are manufactured by using as starting materials 1-(aminophenyl)-3-sulphomethyl-pyrazol-(5)-ones or 1-(nitrophenyl)-3-sulphomethylpyrazol-(5)-ones, in which the nitro group is reduced to the amino group, and acylating these before or after the coupling with acylating agents which contain a fibre-reactive radical.

The halides or anhydrides of organic acids which contain easily replaceable atoms or groups of atoms are, in particular, possible acylating agents which contain easily replaceable atoms or groups of atoms.

The following may be mentioned as examples of acylating agents containing a fibre-reactive radical: chloroacetyl chloride or bromoacetyl chloride, β-chloropropionyl or β-bromopropionyl chloride, α,β-dichloropropionyl or α,β-dibromopropionyl chloride, chloromaleic anhydride, carbyl sulphate, acrylyl chloride, β-chloroacrylyl or β-bromoacrylyl chloride, α-chloroacrylyl or α-bromoacrylyl chloride, α,β-dichloroacrylyl or α,β-dibromoacrylyl chloride, trichloroacrylyl chloride, chlorocrotonyl chloride, propiolic acid chloride, 3,5-dinitro-4-chlorobenzene-sulphonic acid chloride or -carboxylic acid chloride, 3-nitro-4-chlorobenzene-sulphonic acid chloride or -carboxylic acid chloride, 2,2,3,3-tetrafluorocyclobutane-1-carboxylic acid chloride, β-chloroethylsulphonyl-endomethylene-cyclohexanecarboxylic acid chloride, acrylsulphonyl-endomethylene-cyclohexanecarboxylic acid chloride and above all heterocyclic acid halides and their derivatives, such as the 2-chlorobenzoxazolecarboxylic acid chlorides, 2-chlorobenzthiazolecarboxylic or -sulphonic acid chlorides and above all the following compounds possessing at least 2 nitrogen atoms as heteroatoms of a 6-membered heterocyclic structure: 4,5-dichloro-1-phenylpyridazonecarboxylic or -sulphonic acid chloride, 4,5-dichloropyridazonepropionic acid chloride, 1,4-dichlorophthalazine carboxylic or -sulphonic acid chloride, 2,3-dichloroquinoxalinecarboxylic or -sulphonic acid chloride, 2,4-dichloroquinazolinecarboxylic or -sulphonic acid chloride, 2-methanesulphonyl-4-chloro-6-methylpyrimidine, tetrachloropyridazine, 2,4-bis-methanesulphonyl-6-methylpyrimidine, 2,4,6-tri- or 2,4,5,6-tetrachloropyrimidine, 2,4,6-tri- or 2,4,5,6-tetrabromopyrimidine, 2-methanesulphonyl-4,5-dichloro-6-methylpyrimidine, 2,4-dichloropyrimidine-5-sulphonic acid, 5-nitro- or 5-cyano-2,4,6-trichloropyrimidine, 2,6-bis-methanesulphonylpyridine-4-carboxylic acid chloride, 2,4-dichloro-5-chloromethyl-6-methyl-pyrimidine, 2,4-dibromo-5-bromomethyl-6-methylpyrimidine, 2,4-dichloro-5-chloromethylpyrimidine, 2,4-dibromo-5-bromomethylpyrimidine, 2,5,6-trichloro-4-methylpyrimidine, 2,6-dichloro-4-trichloromethylpyrimidine or especially 2,4-dimethylsulphonyl-5-chloro-6-methylpyrimidine, 2,4,6-trimethylsulphonyl-1,3,5-triazine, 2,4-dichloropyrimidine, 3,6-dichloropyridazine, 3,6-dichloropyridazine-5-carboxylic acid chloride, 2,6-dichloro- or 2,6-dibromo-4-carboethoxypyrimidine, 2,4,5-trichloropyrimidine, 2,4-dichloropyrimidine-6-carboxylic acid chloride, 2,4-dichloropyrimidine-5-carboxylic acid chloride, 2,6-dichloro- or 2,6-dibromopyrimidine-4- or -5-carboxylic acid amides or -sulphonic acid amides or -4- or -5-sulphonic acid chloride, 2,4,5,6-tetrachloropyridazine, 5-bromo-2,4,6-trichloropyrimidine, 5-acetyl-2,4,6-trichloropyrimidine, 5-nitro-6-methyl-2,4-dichloropyrimidine, 2-chlorobenzthiazole-6-carboxylic acid chloride, 2-chlorobenzthiazole-6-sulphonic acid chloride, 5-nitro-6-methyl-2,4-dichloropyrimidine, 2,4,6-trichloro-5-chloropyrimidine, 2,4,5,6-tetrafluoropyrimidine, 4,6-difluoro-5-chloropyrimidine, 2,4,6-trifluoro-5-chloropyrimidine, 2,4,5-trifluoropyrimidine, 2,4,6-trichloro-(-tribromo- or -trifluoro)-1,3,5-triazines, as well as 4,6-dichloro(dibromo- or -difluoro)-1,3,5-triazines which are substituted in the 2-position by an aryl or alkyl radical, for example a phenyl, methyl or ethyl radical, or by the radical of an aliphatic or aromatic mercapto compound bonded via the sulphur atom, or by the radical of an aliphatic or aromatic hydroxy compound bonded via the oxygen atom, or, in particular, by an NH$_2$ group or by the radical of an aliphatic, heterocyclic or aromatic amino compound bonded via the nitrogen atom. As such compounds, the radicals of which can be bonded in the 2-position to the triazine nucleus by reaction with trihalotriazines, the following may for example be mentioned: aliphatic or aromatic mercapto or hydroxy compounds, such as thioalcohols, thioglycolic acid, thiophenols, alkoxyalkanols, methyl alcohol, ethyl alcohol or isopropyl alcohol, glycolic acid, phenol, chlorophenols or nitrophenols, phenolcarboxylic and phenolsulphonic acids, naphthols, naphtholsulphonic acids and the like, but in particular ammonia and compounds containing amino groups which can be acylated, such as hydroxylamine, hydrazine, phenylhydrazine, phenylhydrazinesulphonic acids, glycolmonoalkyl ethers, methylamine, ethylamine, isopropylamine, methoxyethylamine, methoxypropylamine, dimethylamine, diethylamine, methylphenylamine, ethylenephenylamine, chloroethylamine, ethanolamines, propanolamines, benzylamine, cyclohexylamine, morpholine, piperidine, piperazine aminocarbonic acid esters, aminoacetic acid ester, aminoethane-sulphonic acid, N-methylaminoethanesulphonic acid, but, above all, aromatic amines, such as aniline, N-methylaniline, toluidines, xylidines, chloroanilines, p- or m-aminocetanilide, aminophenols, anisidine, phenetidine and, in particular, anilines containing acid groups, sulphanilic acid, methanilic acid, orthanilic acid, anilinedisulphonic acid, aminobenzylsulphonic acid, anilinemethanesulphonic acid, aminobenzenedicarboxylic acids, naphthylaminomonosulphonic, -disulphonic and -trisulphonic acids, aminobenzoic acid, such as 2-hydroxy-5-aminobenzoic acid, and in addition also coloured compounds, or compounds with dyestuff character, for example 4-nitro-4'-aminostilbenedisulphonic acid, 2-nitro-4'-aminodiphenylamino-4,3'-stilbene-disulphonic acid, 2-nitro-4'-aminodiphenylamine-4,3'-disulphonic acid and, in particular, aminoazo dyestuffs or aminoanthraquinones or phthalocyanines which still contain at least one reactive amino group.

The introduction of the substituent in the 2-position of the triazine radical can also be effected after the condensation with the starting diamine or after the reaction, according to the invention, to give the azo compound with the radical of the formula (1).

In addition to the fibre-reactive radicals which can be introduced by acylation, further such radicals which may be mentioned are, for example, the vinylsulphone, the β-sulphato- or thiosulphatoethylsulphone, β-thiosulphatopropionylamide, the β-thiosulphatoethylsulphonylamide or the sulphonic acid-N,β-sulphatoethylamide groups, which are introduced into the diazo component in another way, for example by ester formation or thioester formation.

As compounds which contain a fibre-reactive radical which cannot be introduced by acylation, and in which the fibre-reactive radical is therefore preferably not bonded via an amino group, but is bonded directly to the benzene radical, the sulpho esters of the following sulphones may, in particular, be mentioned: 1-amino-2-methoxy-5-(β-hydroxyethyl)-phenylsulphone, 1-amino-benzene-3- or 4-β-hydroxyethylsulphone, 1-amino-2-methyl-benzene-5-β-hydroxyethylsulphone, 1-amino-4-(β-hydroxyethylsulphonylpropionylaminomethyl)-benzene, 1-amino-4-(β-hydroxyethylsulphonylamino)-benzene, as well as reactive compounds which can be obtained via the appropriate methylols by Einhorn's method, for example 1-amino-4-chloroacetylaminomethyl-benzene or 1-amino-3-chloroacetylaminomethyl-benzene-6-sulphonic acid.

The condensation with the acid halides or anhydrides, or with the heterocyclic halogen compounds, is advantageously carried out in the presence of acid acceptors, for example sodium carbonate. It is to be understood that all these reactions are to be carried out in such a manner that an unsaturated bond or at least a replaceable halogen atom still remains in the final product.

The azo compounds obtainable according to the present process and its different variants, as well as their heavy metal complexes, are new; they are suitable for dyeing and printing widely different types of materials, such as, for example, silk, leather, wool, synthetic fibres of polyamides and polyurethanes, polyester fibres or polyacrylonitrile fibres, and polyhydroxylated materials, for example cellulose-containing materials of fibrous structure, such as linen, cellulose, regenerated cellulose, cotton and the like.

The non-metallised azo compounds according to the invention are particularly important as dyestuffs.

However, the most important compounds are those azo compounds according to the invention which contain a reactive radical and a water-solubilising group, in particular a sulphonic acid group. These dyestuffs are preferably used for dyeing nitrogen-containing fibres, such as, for example, of super polyamides, super polyurethanes, silk, leather and in particular wool, for example from weakly acid, neutral or weakly alkaline baths, optionally with the addition of customary assistants, for example ethylene oxide condensation products of high molecular weight amines, and, above all, for dyeing cellulose materials, in particular cotton, for example by the exhaustion process from a dilute liquor, from alkaline baths optionally having a high salt content, and in particular by the pad-dyeing process, in which the article is impregnated with aqueous dyestuff solutions which optionally also contain salt, and the dyestuffs are fixed after an alkali treatment or in the presence of alkali, optionally with the action of heat.

The water-soluble reactive dyestuffs according to the invention show an excellent boid-up capacity. They are also suitable for printing, in particular on cotton, and also for printing nitrogen-containing fibres, for example of wool, silk or fibre blends containg wool.

The dyeings and prints are distinguished by interesting and valuable yellow, very pure and brilliant shades. The dyeings and prints exhibit a good stability to acids and alkalis, and a good stability to synthetic resin finishing agents, have a good fastness to light and, in particular on cotton, an outstanding fastness to wet processing. The light degree of fixation and the easy removability of non-fixed dyestuff is also deserving of mention.

In order to improve the fastness to wet processing, it is advisable to rinse the dyeings and printings obtained thoroughly with cold and hot water, optionally with the addition of an agent which has a dispersing effect and promotes the diffusion of the non-fixed material.

In the examples which follow, the parts, unless otherwise indicated, denote parts by weight, and the percentages denote percentages by weight. The relationship of parts by weight to parts by volume is the same as of the gram to the cm$^3$.

EXAMPLE 1

A solution of 18.5 parts of cyanuric chloride in 50 parts of acetone is poured into a neutralised solution of 17.3 parts of 1-aminobenzene-3-sulphonic acid in 100 parts of water and 100 parts of ice and during the condensation the pH is maintained at 6 to 7 by the dropwise addition of 2N sodium hydroxide solution. Upon completion of the condensation a neutral solution of 18.8 parts of 1,3-diaminobenzene-4-sulphonic acid is added, the solution is heated to 20°–25° C. and the pH maintained is at 6 to 7 by the dropwise addition of 2N sodium hydroxide solution. As soon as no more diaminobenzenesulphonic acid can be detected in the mixture, 7 parts of sodium nitrite are added and when this has dissolved, the solution is poured on a mixture of 200 parts of ice and 25 parts of concentrated hydrochloric acid. The yellow suspension of the diazo compound is stirred for 1 hour in an ice bath, then a slight excess of nitrous acid is annulled by the addition of sulphamic acid. A solution of 27.6 parts of 1-phenyl-3-sulphomethyl-pyrazolone-(5) in 100 parts of water is then poured into this diazo solution. The pH, which is initially 1.5, is raised to 6.5 by the dropwise addition of sodium hydroxide solution, when a clear yellow solution is obtained. This solution is stirred for 1 hour in an ice bath the pH is adjusted to 7, and the dyestuff is precipitated by addition of sodium chloride. The resulting dyestuff dyes cotton in pure yellow shades.

Further yellow dyestuffs are obtained when, in accordance with the directions of Example 1, the amines listed in column 1 of the following Table are condensed with cyanuric chloride, the resulting monocondensation products are condensed with the diamines listed in column II, diazotised, and coupled with the coupling components listed in column III.

| | I<br>Amine | II<br>Diamine | III<br>Coupling Component |
|---|---|---|---|
| 1 | 1-aminobenzene-3-sulphonic acid | 1,33-phenylendiamine-4-sulphonic acid | 3-sulphomethyl-pyrazolone-(5) |
| 2 | " | " | 1-methyl-3-sulpho-methylpyrazolone-(5) |
| 3 | 1-aminobenzene-2-sulphonic acid | " | 1-(2'-chlorophenyl)-3-sulphomethyl-pyrazolone (5) |
| 4 | " | " | " |
| 5 | 1-aminobenzene-2-sulphonic acid | 1,3-phenylen-diamine-4-sulphonic acid | 1-(2'-sulphophenyl)-3-sulphomethyl-pyrazolone-(5) |

-continued

| | I<br>Amine | II<br>Diamine | III<br>Coupling Component |
|---|---|---|---|
| 6 | 1-aminobenzene-4-sulphonic acid | " | 1-(3'-sulphophenyl)-3-sulphomethyl-pyrazolone-(5) |
| 7 | " | " | 1-ethyl-3-sulphomethyl-pyrazolone-(5) |
| 8 | 1-aminobenzene-2,4-disulfonic acid | " | 1-propyl-3-sulphomethyl-pyrazolone-(5) |
| 9 | 1-aminobenzene-2,5-disulphonic acid | 1,4-phenylene-diamine-2-sulphonic acid | 1-(4'-nitrophenyl)-3-sulphomethyl-pyrazolone-(5) |
| 10 | 1-aminobenzene-3,5-disulphonic acid | 1,3-phenylene-diamine | 3-sulphomethyl-pyrazolene-(5) |
| 11 | 1-naphthylamine-5-sulphonic acid | 1,3-phenylene-diamine-4,6-disulphonic acid | 3-sulphomethyl-pyrazolone-(5) |
| 12 | 1-naphthylamine-6-sulfonic acid | " | " |
| 13 | 1-naphthylamine-7-sulphonic acid | " | " |
| 14 | 1-naphthylamine-5,7-disulphonic acid | 1,4-phenylene-diamine-2,5-disulphonic acid | 1-(2'-methylphenyl)-3-sulphomethyl-pyrazolone-(5) |
| 15 | 4-aminobenzyl-sulphonic acid | 1,3-phenylene-diamine-4-sulphonic acid | 1-(2'-cyanoethyl)-3-sulphomethyl-pyrazolone-(5) |
| 16 | 2-amino-5-sulphobenzoic acid | " | 1-(2'-methoxyethyl)-3-sulphomethyl-pyrazolone-(5) |
| 17 | 4-aminobenzoic acid | 1,3-phenylene-diamine-4,6-disulphonic acid | 1-(4'-methylphenyl)-3-sulphomethyl-pyrazolone-(5) |
| 18 | 2-aminobenzoic acid | " | 1-2',5'-dimethylphenyl)-3-sulphomethyl-pyrazolone-(5) |
| 19 | 1-aminobenzene-3-and-4-sulphonic acid | 1,3-phenylene-diamine-4-sulphonic acid | 3-sulphomethyl-pyrazolone-(5) |
| 20 | 1-aminobenzene-4-β-chloroethyl-sulphone | " | 1-benzyl-3-sulphomethyl-pyrazolone-(5) |
| 21 | 1-amine-3-chloro-acetylaminomethyl-benzene-6-sulphonic acid | " | 1-cyclohexyl-3-sulphomethyl-pyrazolone-(5) |
| 22 | aniline-N-ω-methane-sulphonic acid | " | 1-(4'-flourophenyl)-3-sulphomethyl-pyrazolone-(5) |
| 23 | 3'-amino-2,4-bis-phenylamino-6-chloro-1,3,5-triazine"-sulphonic acid | 1,3-phenylene-diamine-4-sulphonic acid | 3-sulphomethyl-pyrazolone-(5) |
| 24 | 3'-amino-2,4-bis-phenylamino-6-chloro-1,3,5-triazine-4',3"-disulphonic acid | 1,3-phenylene-diamine-4-sulphonic acid | 3-sulphomethyl-pyrazolone-(5) |
| 25 | 1-aminobenzene-3-sulphonic acid | 1,3-phenylene-diamine-4-sulphonic acid | 1-(2'-chloro-5'-sulphophenyl)-3-sulphomethyl-pyrazolone-(5) |
| 26 | 1-aminobenzene-2-sulphonic acid | " | 1-(4',8'-disulphonapth-2'-yl)-3-sulphomethyl-pyrazolone-(5) |
| 27 | aniline-N-ω-methanesulphonic acid | " | 1-(4'-sulphophenyl)-3-sulphomethyl-pyrazolone-(5) |
| 28 | aniline | " | 3-sulphomethylpyrazolone-(5)<br>" |
| 29 | 1-aminobenzene-3-sulphonic acid | 2,6-diamino-naphthalene-4,8-disulphonic acid | |

EXAMPLE 2

9.4 Parts of 1,3-diaminobenzene-4-sulphonic acid are suspended in 100 parts of water and dissolved by addition of alkali to a pH of 7. To this solution are added at room temperature and with good stirring 10.4 parts of 2-isopropoxy-4,6-dichloro-1,3,5-triazine and the pH is maintained at 6-7 during the condensation by the dropwise addition of 2N sodium hydroxide solution.

Upon completion of the condensation, the condensation mixture is cooled to 0° C., 13 parts by volume of concentrated hydrochloric acid are added, and diazotisation is carried out by the dropwise addition of 50 parts of n-sodium nitrite solution. A solution of 8.9 parts of 3-sulphomethyl-pyrazolone-(5) in 40 parts of water is poured into the resulting diazo suspension and the coupling mixture is adjusted to pH 7 by the dropwise addition of 5N sodium hydroxide solution within 1 hour. The dyestuff is isolated from the yellow dyestuff solution by addition of potassium chloride. It dyes cotton in fast yellow shades.

Further yellow dyestuffs having similar properties are obtained if the compound listed in column II of the following Table is used as diamine, that listed in column I as acylating agent, and that listed in column III as coupling component.

| | I | II | III |
|---|---|---|---|
| 1 | 2,4-dichloro-6-methoxy-1,3,5-triazine | 1,3-phenylene-diamine-4-sulphonic acid | 3-sulphomethyl-pyrazolone-(5) |
| 2 | 2-amino-4,6-dichloro-1,3,5-triazine | " | 1-methyl-3-sulphomethyl-pyrazolone-(5) |
| 3 | 2-(2'-ethoxy)-ethoxy-4,6-dichloro-1,3,5-triazine | 1,3-phenylene-diamine-4-sulphonic acid | 1-ethyl-3-sulphomethylpyrazolone-(5) |
| 4 | 2,4,5,6-tetrachloropyrimidine | " | 1-cyclohexyl-3-sulphomethyl-pyrazolone-(5) |
| 5 | 2,3-dibromopropionic chloride | 1,4-phenylene-diamine-3-sulphonic acid | 1-benzyl-3-sulphomethyl-pyrazolone-(5) |
| 6 | 2,4-dichloropyrimidine-5-carboxylic acid chloride | 2,4-diamino-5-sulpho-benzoic acid | 1-phenyl-3-sulphomethyl-pyrazolone-(5) |
| 7 | 2,4-dichloro-6-phenyl-1,3,5-triazine | 1,3-diamino-benzene-4,6-disulphonic acid | 1-(4'-methylphenyl)-3-sulphomethyl-pyrazolone-(5) |
| 8 | 2,4-dichloro-6-[5'-("-chloro-6"-amino)-1,3,5-triazine-2"-yl-amino]-phenyl-amino-1,3,5-triazine-2'-sulphonic acid | 1,3-phenylene-diamine-4-sulphonic acid | 1-(2'-methylphenyl)3-sulphomethyl-pyrazolone-(5) |
| 9 | chloroacetyl chloride | " | 1-(3'-sulphophenyl)-3-sulphomethyl-pyrazolone-(5) |
| 10 | α-bromoacrylic chloride | " | 1-(2',5'-dichloro-phenyl)-3-sulphomethyl-pyrazolone-(5) |
| 11 | 3,5-dinitro-4-chlorobenzene-sulphonic acid chloride | 1,3-diamino-benzene-4,6-disulphonic acid | 3-sulphomethyl-pyrazolone-(5) |
| 12 | 2,2,3,3-tetrafluorocyclobutane-1-carboxylic acid chloride | " | 1-(1'-acetaminophenyl)-3-sulphomethyl-pyrazolone-(5) |
| 13 | β-chloroethyl-sulphonyl-endo-methylene-cyclohexanecarboxylic acid chloride | 2,4-diamino-toluene-5-sulphonic acid | 1-(2'-chlorophenyl)-3-sulphomethyl-pyrazolone-(5) |
| 14 | 2-chlorobenzthiazole-carboxylic acid chloride | 1,4-diamino-5-chlorobenzene-2-sulphonic acid | 1-(4'-bromophenyl)-3-sulphomethyl-pyrazolone-(5) |
| 15 | 4,5-dichloropyridazone-propionic chloride | 1,4-diamino-benzene-2,5-disulphonic acid | 3-sulphomethyl-pyrazolone-(5) |
| 16 | 2,3-dichloro-quinoxaline-6-sulphonic acid chloride | 1,4-diamino-benzene-2,6-disulphonic acid | " |
| 17 | 2-methanesulphonyl-4-chloro-6-methyl-pyrimidine | " | 1-methyl-3-sulphomethyl-pyrazolone-(5) |
| 18 | 2,4,6-tribromopyrimidine | 1,3-diamino-benzene-4-sulphonic acid | " |
| 19 | 2-methanesulphonyl-4,5-dichloro-6-methyl-pyrimidine | 1,3-diamino-benzene-4-sulphonic acid | 1-phenyl-3-sulphomethyl-pyrazolone-(5) |
| 20 | 5-cyano-2,4,6-trichloro-pyrimidine | " | 3-sulphomethyl-pyrazolone-(5) |
| 21 | 2,6-bismethane-sulphonylpyridine-4-carboxylic acid chloride | " | " |
| 22 | 2,4-dichloro-5-chloromethyl-6-methylpyrimidine | " | " |
| 23 | 2,4-bismethyl-sulphonyl-5-chloro-6-methyl-pyrimidine | " | 1-(2'-sulphophenyl)-3-sulphomethyl-pyrazolone-(5) |
| 24 | 2,4,6-trimethyl-sulphonyl-1,3,5-triazine | 1,4-diamino-benzene-2,6-disulphonic acid | 1-(2'-sulphophenyl)-3-sulphomethyl-pyrazolone-(5) |
| 25 | 3,6-dichloropyridazine-5-carboxylic acid chloride | 1,4-diamino-benzene-2,6-disulphonic acid | 1-ethyl-3-sulphomethyl-pyrazolone-(5) |
| 26 | 2,4-dichloropyrimidine-6-carboxylic acid chloride | 1,3-diamino-benzene-4,6-disulphonic acid | 1-phenyl-3-sulphomethyl-pyrazolone-(5) |
| 27 | 2,4,5,6-tetra-chloro-pyridazine | 1,3-diamino-benzene-4,6-disulphonic acid | 3-sulphomethyl-pyrazolone-(5) |
| 28 | 2,4,5,6-tetra-fluoropyrimidine | 1,3-diamino-benzene-4-sulphonic acid | " |
| 29 | 2,4,6-trifluoro-5-chloropyrimidine | " | " |
| 30 | 2,4,6-trichloro-1,3,5-triazine | " | " |
| 31 | 2,4-dichloro-6-methylmercapto-1,3,5-triazine | " | 1-methyl-3-sulphomethyl-pyrazolone-(5) |
| 32 | 2,4-dichloro-6-ethyl-1,3,5-triazine | 1,3-diamino-benzene-4,6-disulphonic acid | 3-sulphomethyl-pyrazolone-(5) |
| 33 | 2,4-dichloro-6-isopropoxy-1,3,5-triazine | " | 1-(3'-sulphophenyl)-3-sulphomethyl-pyrazolone-(5) |
| 34 | " | 1,3-diamino-benzene-4-sulphonic acid | 1-(2'-chloro-5'-sulphophenyl)-3-sulphomethyl-pyrazolone-(5) |
| 35 | " | 1,4-phenylene-diamine-3-sulphonic acid | 1-(2'-chloro-6'-methyl-4'-sulphophenyl)-3-sulphomethyl-pyrazolone-(5) |
| 36 | 2-amino-4,6-dichloro-1,3,5-triazine | 1,3-diamino-benzene-4-sulphonic acid | 3-sulphomethyl-pyrazolone-(5) |
| 37 | 2,4,6-trichloro-1,3,5-triazine | " | 1-(4'-sulphophenyl)-3-sulphomethyl-pyrazolone-(5) |
| 38 | 2,4-dichloro-6-isopropoxy-1,3,5-triazine | 1,3-diamino-benzene-4-sulphonic acid | 1-(2'-hydroxyethyl)-3-sulphomethyl-pyrazolone-(5) |
| 39 | 2,4,6-trifluoro-5-chloropyrimidine | " | 1-phenyl-3-sulphomethyl-pyrazolone-(5) |
| 40 | 2,4,6-tribromo-1,3,5-triazine | " | 1-(2-'-methoxyphenyl)-3-sulphomethyl-pyrazolone-(5) |
| 41 | 2-ethylamino-4,6-dichloro-triazine | " | 3-sulphomethyl-pyrazolone-(5) |
| 42 | 2-morpholine-4,6-dichloro-triazine | " | " |
| 43 | 2-ureido-4,6-dichlorotriazine | " | " |
| 44 | 2-dimethylamino-sulphonylamino-4,6-dichloro-triazine | " | " |

EXAMPLE 3

To a neutral aqueous solution containing 35.8 parts of the sodium salt of 2-(3'-aminophenyl)amino-4,6-dichloro-1,3,5-triazine-4'-sulphonic acid are added 25 parts by volume of a 4N sodium nitrite solution. The whole mixture is cooled to 0° C. and 25 parts by volume of concentrated hydrochloric acid are tipped in all at once. Upon completion of the diazotisation, a slight excess of nitrous acid is annulled by addition of sulphamic acid. Into the suspension of the diazo compound is then poured an aqueous solution containing 20 parts of the sodium salt of 3-sulphomethylpyrazolone-(5). The diazo compound passes into solution and a clear yellow dyestuff solution is formed. The pH is adjusted to 7 and then a neutral aqueous solution of 21 parts of the sodium salt of 1,3-phenylenediamine-4-sulphonic acid is added. Condensation is carried out at 20°-25° C., in the course of which the pH of the solution is maintained at 6-7 by the dropwise addition of sodium hydroxide solution. Upon completion of the condensation, the solution is cooled to 0° C. and treated with a solution of 18.5 parts of cyanuric chloride in 50 parts of acetone. Condensation is carried out at 0°-5° C., the pH being maintained at 6-7 by the dropwise addition of sodium hydroxide solution. Upon completion of the condensation, 25 parts by volume of a 20% aqueous ammonia solution is added and the batch is stirred for 3 hours at 40° C. The dyestuff of the formula

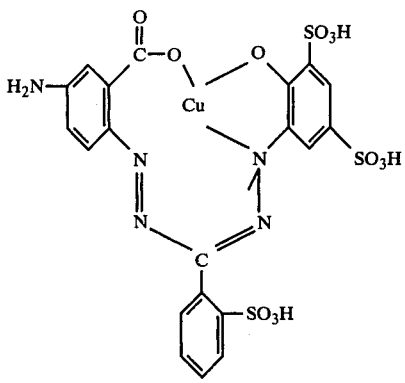

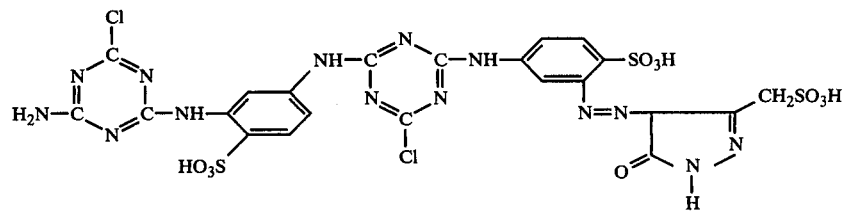

is salted out with sodium chloride, then filtered and dried. It dyes cellulose fibres in fast yellow shades.

EXAMPLE 4

Diazotisation and coupling is carried out as described in Example 3. To the neutral dyestuff solution, which contains the dyestuff of the formula

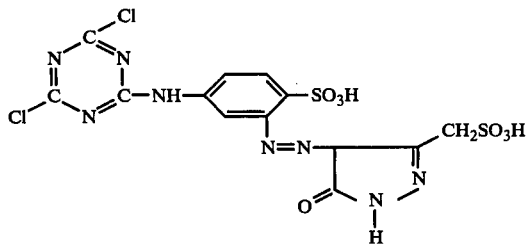

is then added a neutral aqueous solution of 53.3 parts of 1-amino-4-(3'-aminophenyl)-aminoanthraquinone-2,4'-disulphonic acid. The mixture is heated to 40°-45° C. and condensation is carried out at this temperature, the pH being maintained at 6-7 by the dropwise addition of sodium hydroxide solution. Upon completion of the condensation, the dyestuff is isolated by addition of sodium chloride. It dyes cellulose fibre fabrics in pure green shades.

If instead of 1-amino-4-(3'-aminophenyl)-aminoanthraquinone-2,4'-disulphonic acid there is used an equivalent amount of the phthalocyanine dyestuff of the formula

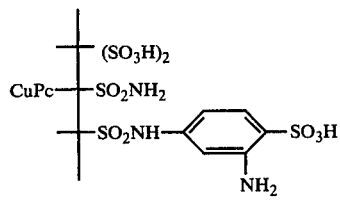

or of the aminoformazane dyestuff of the formula there are obtained likewise dyestuffs which dye cellulose fibre fabrics in fast green shades.

EXAMPLE 5

20 Parts of 1-ethyl-3-aminocarbonyl-4-methyl-6-hydroxy-pyridone-2 in the form of the sodium salt are dissolved in 50 parts of 2N sodium hydroxide solution. The resulting solution is treated with 52 parts of an aqueous solution of the bisulphite adduct of formaldehyde (prepared by 17.3 parts of 2-aminobenzenesulphonic acid are dissolved in 100 parts of water with the addition of 5.5 parts of anhydrous sodium carbonate. The resulting solution is treated with 25 parts by volume of 4N sodium nitrite solution and the entire solution is poured on a mixture of 100 parts of ice and 25 parts by volume of concentrated hydrochloric acid. The suspension of the diazo compound is adjusted to a pH of 8.5 by addition of 10% sodium carbonate solution. 110 Parts by volume of an aqueous solution containing 31.2 parts of the sodium salt of 1-ethyl-3-sulphomethyl-4-methyl-5-aminocarbonyl-6-hydroxy-pyrid-(2)-one are then added and the pH of the reaction mixture is maintained at 8.5 to 9 during the coupling. Upon completion of the coupling, the dyestuff is precipitated from the yellow dyestuff solution by addition of sodium chloride. It dyes fabrics of synthetic polyamide material in fast greenish yellow shades.

Further dyestuffs which dye fabrics in the shade indicated in column III of the following Table are obtained according to the directions of the Example by diazotising the diazo components listed in column I and coupling them with the coupling components listed in column II.

| | I | II | III |
|---|---|---|---|
| 1 | aminobenzene | 3-sulphomethyl-pyrazolone-(5) | yellow on polyamide |
| 2 | 1-amino-4-chloro-benzene | 1-phenyl-3-sulpho-methylpyrazolone-(5) | " |
| 3 | 1-amino-4-nitro-benzene | 1-methyl-3-sulpho-methylpyrazolone-(5) | " |
| 4 | 1-amino-4-methyl- | 1-cyclohexyl-3-sulpho- | " |

-continued

| I | II | III |
|---|---|---|
| sulphonylbenzene | methyl-pyrazolone-(5) | |
| 5 1-amino-2-tri-fluoromethyl-4-chlorobenzene | 1-ethyl-3-sulpho-methylpyrazolone-(5) | " |
| 6 1-amino-2-chloro-4-methylsulpho-nylbenzene | 3-sulphomethyl-pyrazolone-(5) | " |
| 7 1-amino-2,4-dicyanobenzene | 1-(2'-chlorophenyl)-3-sulphomethyl-pyrazolone-(5) | " |
| 8 4-aminbobenzoic-cyclohexyl ester | 1-(3'-acetylamino-phenyl)-3-sulpho-methyl-pyrazolone-(5) | " |
| 9 1-aminonaphthal-ene-6-sulphonic acid-N,γ-isopro-pyloxypropyl-amide | " | " |
| 10 1-aminobenzene-4-sulphonic acid -N-isopropylamide | 3-sulphomethyl-parazolone-(5) | yellow on polyamide |
| 11 4-amionophenyl-sulphamate | 1-(2'-methylphenyl)-3-sulphomethyl-pyrazolone-(5) | " |
| 12 2-aminothiazole | 3-sulphomethyl-pyrazolone-(5) | " |
| 13 2-aminoquinoline | 3-sulphomethyl-pyrazolone-(5) | " |
| 14 2-amino-6-methyl-benzthiazole | " | orange on polyamide |
| 15 2-amino-1,3,5-thiadiazole | " | " |
| 16 3-aminobenziso-thiazole | 1-(3'-sulphophenyl)-3-sulphomethyl-pyrazolone-(5) | " |
| 17 4-aminoazobenzene | 3-sulphomethyl-pyrazolone-(5) | " |
| 18 4-aminoazobenzene-3'-sulphonic acid | 1-(4'-chlorophenyl)-3-sulphomethyl-pyrazolone-(5) | " |
| 19 4-(6',8'-disulpho-naphth-2'-ylazo)-3-methylaniline | 3-sulphomethyl-pyrazolone-(5) | " |
| 20 sulphanilic acid | 1-benzyl-3-sulpho-methyl-pyrazolone-(5) | yellow on polyamide |
| 21 2-naphthylamine-1-sulphonic acid | 1-propyl-3-sulpho-methyl-pyrazolone-(5) | yellow on polyamide |
| 22 1-amino-4-(β-sulphatoethyl-sulphonyl)-benzene | " | " |
| 23 1-amino-4-(β-sulphatoethyl-sulphonamido)-benzene | " | " |

EXAMPLE 6

15.4 Parts of 5-nitro-2-amino-1-hydroxybenzene are dissolved with warming in 120 parts of water and 15 parts of 30% hydrochloric acid. The resulting solution is cooled to 5° C. and diazotised at 5° to 10° C. by the dropwise addition of 25 parts of 4 normal sodium nitrite solution.

22.5 Parts of 1-phenyl-3-sulphomethyl-5-pyrazolone are dissolved with neutral reaction in 100 parts of water of 20° C. and the solution is treated with 50 parts of a 4 normal sodium acetate solution. After it has been cooled to 5° C., the above diazo suspension is added with stirring and the orange yellow coupling mixture is brought to neutral to slightly alkaline reaction by the dropwise addition of 2 normal sodium carbonate solution. The coupling is terminated after several hours. The partly precipitated dyestuff is completely precipitated by addition of sodium chloride, filtered off, and washed with dilute sodium chloride solution. It has the following constitution:

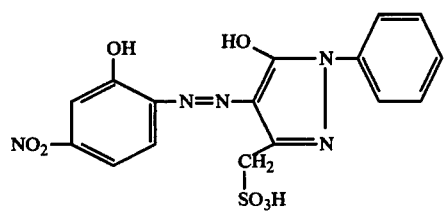

38.7 parts of the resulting dyestuff in the form of the filter paste are suspended in 600 parts of water of 50° C. Upon addition of 25 parts of basic chromium sulphate the metallising mixture is treated with 50 parts of 2 normal sulphuric acid and subsequently stirred in an autoclave for 12 hours at 120°–125° C. After the batch has cooled to 60° C. the 1:1 chromium complex obtained in the form of crystals of a greenish bronze cast is filtered off, washed with dilute sodium chloride solution until it shows neutral reaction, and dried. By grinding the product with a small quantity of sodium carbonate a dyestuff is obtained which, from a strongly sulphuric acid, bath dyes wool in pure, bluish red shades with very good fastness to light.

EXAMPLE 7

44.0 Parts of the 1:1 chromium complex (obtained by the known process and containing 1 atom of chromium for each molecule of monoazo dyestuff) of the azo dyestuff from diazotised 5-nitro-2-amino-1-hydroxybenzene and 1-phenyl-3-sulphomethyl-5-pyrazolone are stirred together in 1000 parts of hot water with 33.9 parts of the monoazo dyestuff obtained by the known process from diazotised 5-nitro-2-amino-1-hydroxybenzene and 1-phenyl-3-methyl-5-pyrazolone. The suspension is adjusted to a pH of 7 to 8 by addition of 20 parts by volume of concentrated sodium hydroxide solution and subsequently stirred at 90°–95° C. until both starting dyestuffs can no longer be detected. The unitary chromium mixed complex present in the clear solution is precipitated by addition of sodium chloride, isolated by filtration, washed with sodium chloride solution, and then dried in vacuo. After it has been ground, the dyestuff is in the form of a red, readily water-soluble powder and from a bath containing ammonium sulphate dyes wool or polyamide fibres in full red shades with good fastness properties. It has the following constitution:

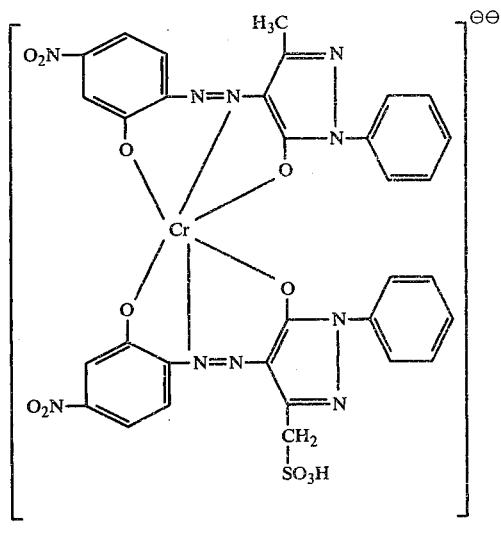

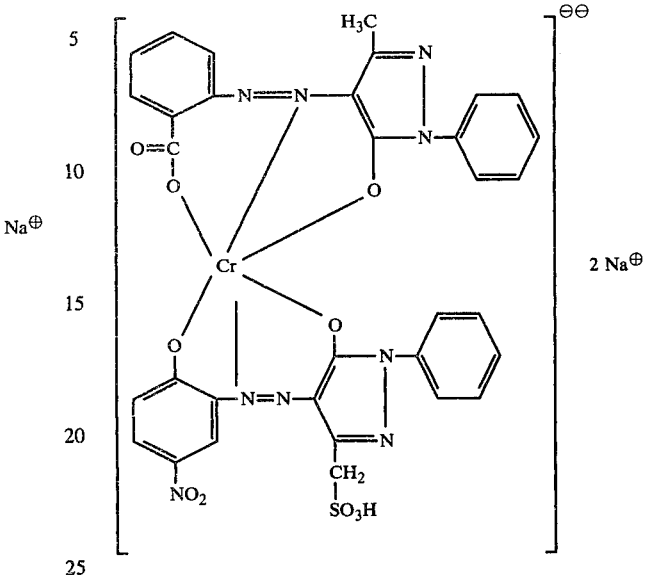

EXAMPLE 8

44.0 Parts of the 1:1 chromium complex (obtained by the known process and containing 1 atom of chromium for each molecule of monoazo dyestuff) of the azo dyestuff from diazotised 4-nitro-2-amino-1-hydroxybenzene and 1-phenyl-3-sulphomethyl-5-pyrazolone are stirred in 1000 parts of hot water together with 32.2 parts of the monoazo dyestuff obtained by the known process from diazotised 1-aminobenzene-2-carboxylic acid and 1-phenyl-3-methyl-5-pyrazolone. The suspension is adjusted to pH 7 to 8 by addition of 20 parts by volume of concentrated sodium hydroxide solution and subsequently stirred at 90°–95° C. until both starting dyestuffs can no longer be detected. The unitary chromium mixed complex present in clear solution is precipitated by the addition of sodium chloride, isolated by filtration, washed with sodium chloride solution, and then dried in vacuo. After it has been ground, the dyestuff is in the form of a red, readily water-soluble powder and from a bath containing ammonium sulphate dyes wool or polyamide fibres in full yellowish orange with good fastness properties. It has the following constitution:

EXAMPLE 9

49.95 Parts of the 1:1 chromium complex (obtained by the known process and containing 1 atom of chromium for each molecule of monoazo dyestuff) of the azo dyestuff from diazotised 4-chloro-2-amino-1-hydroxybenzene and 1-phenyl-3-sulphomethyl-5-pyrazolone are stirred in 1000 parts of hot water together with 29.85 parts of the monoazo dyestuff obtained by the known process from diazotised 4-chloro-2-amino-1-hydroxybenzene and 2-hydroxynaphthalene. The suspension is adjusted to pH 7 to 8 by addition of 20 parts by volume of concentrated sodium hydroxide solution and subsequently stirred at 90°–95° C. until both starting dyestuffs can no longer be detected. The unitary chromium mixed complex present in clear solution is precipitated by the addition of sodium chloride, isolated by filtration, washed with sodium chloride solution, and then dried in vacuo. After it has been ground, the dyestuff is in the form of a dark red, readily water-soluble powder and from a bath containing ammonium sulphate dyes wool or polyamide fibres in full brown shades with good fastness properties. It has the following constitution:

EXAMPLE 10

45.4 Parts of the 1:1 chromium complex (obtained by the known process and containing 1 atom of chromium for each molecule of monoazo dyestuff) of the azo dyestuff from diazotised 6-nitro-4-methyl-2-amino-1-hydroxybenzene and 1-phenyl-3-sulphomethyl-5-pyrazolone are stirred in 1000 parts of hot water together with 33.9 parts of the monoazo dyestuff obtained by the known process from diazotised 4-nitro-2-amino-1-hydroxybenzene. The suspension is adjusted to pH 7 to 8 by addition of 20 parts vy volume of concentrated sodium hydroxide solution and subsequently stirred at 90°–95° C. until both starting dyestuffs can no longer be detected. The unitary chromium mixed complex present in clear solution is precipitated by the addition of sodium chloride, isolated by filtration, washed with sodium chloride solution, and then dried in vacuo. After it has been ground, the dyestuff is in the form of a dark red, readily water-soluble powder from a bath containing ammonium sulphate dyes wool or polyamide fibres in full scarlet shades with good fastness properties. It has the following constitution:

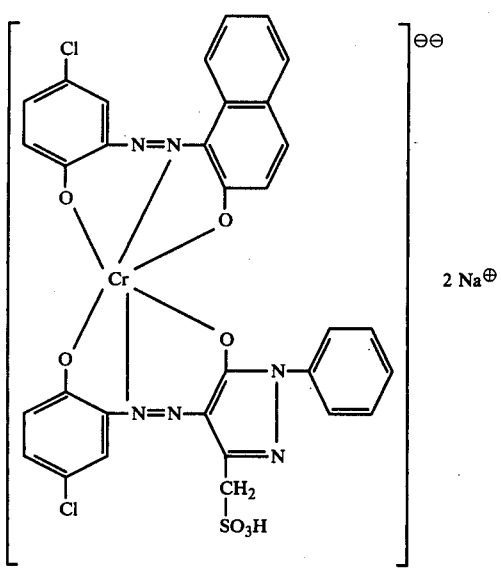

EXAMPLE 11

15.4 Parts of 4-nitro-2-amino-1-hydroxybenzene are dissolved with warming in 120 parts of water and 15 parts of 30% hydrochloric acid. The resulting solution is cooled to 5° C. and diazotised at 5° to 10° C. by the dropwise addition of 25 parts of 4 normal sodium nitrite solution.

23.9 Parts of 1-(2'-methyl-phenyl)-3-sulphomethyl-5-pyrazolone are dissolved with neutral reaction in 100 parts of water of 20° C. and the solution is treated with 50 parts of a 4 normal sodium acetate solution. After it has been cooled to 5° C., the above diazo suspension is added with stirring and the orange-yellow coupling mixture is brought to neutral to slightly alkaline reaction by the dropwise addition of 2 normal sodium carbonate solution. The coupling is terminated after several hours. The partially precipitated dyestuff is completely precipitated by addition of sodium chloride, filtered off, and washed with dilute sodium chloride solution. It has the following constitution:

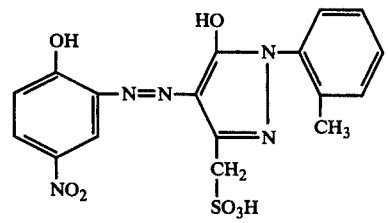

39.4 Parts of the above obtained dyestuff are suspended in 600 parts of water of 70°–80° C. and dissolved by addition of 20 parts of 30% sodium hydroxide solution. At constant temperature this solution is treated with a solution of 15 parts of crystallised cobalt-II-sulphate and 15 parts of tartaric acid in 200 parts of water of 70°–80° C. The symmetrical 1:2 cobalt complex forms with the change in colour from brownish red to brownish yellow; it is precipitated from the solution by addition of sodium chloride, isolated by filtration, washed with dilute sodium chloride solution, and then dried. After it has been ground, the resulting new dyestuff is in the form of a brownish powder and from a slightly acid

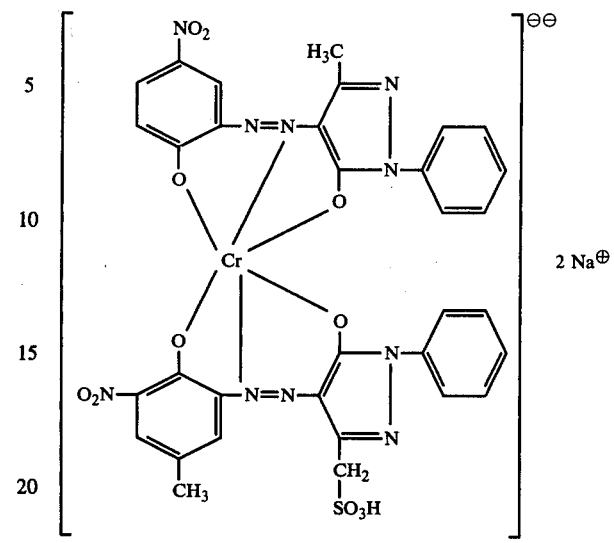

bath in the presence of suitable assistants dyes woollen fabric in full, fast brownish yellow shades. The symmetrical 1:2 chromium complex, which dyes woollen fabric in the same dyeing process in full, yellowish orange shades, is obtained by metallising 39.4 parts of the above dyestuff with 130 parts of an aqueous solution of sodium disalicylatochromiate-III which contains 3.07 percent by volume of $Cr_2O_3$, by stirring the mixture for several hours under reflux.

EXAMPLE 12

26.7 Parts of the dyestuff of the formula

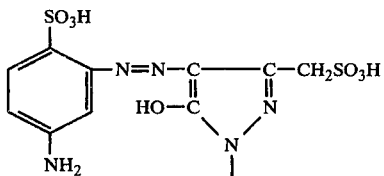

manufactured by coupling 11.5 parts of 2-amino-4-acetylaminobenzenesulphonic acid with 16.7 parts of 1-(3'-sulphophenyl)-3-sulphomethyl-pyrazolone-5-and subsequent saponification of the product in 4% sodium hydroxide solution, are dissolved in 250 parts of water with the addition of sodium hydroxide solution at pH 7. The solution is cooled to 0° C., 9.25 parts of cyanuric chloride are added, and condensation is carried out at the indicated temperature, in the course of which the reaction mixture is kept neutral by the gradual dropwise addition of 2 normal sodium hydroxide solution. Upon completion of the condensation a solution of 2.7 parts of 1,4-diaminobenzene is added, the batch is heated to 30° C. and at pH 6.5 to 7 this temperature is kept until the condensation is terminated. The resulting yellow dyestuff solution is evaporated to dryness in vacuo. The resulting dyestuff powder dyes cotton in fast yellow shades in the exhaustion process. Further yellow dyestuffs suitable for use in the exhaustion process are obtained by using instead of 1,4-diaminobenzene equivalent amounts of 1,3-diaminobenzene, 1,3-diaminobenzene-4-sulphonic acid, 1,4-diaminobenzene-3-sulphonic acid, 4,4'-diaminodiphenylurea, 4,4'-siaminostilbene-disulphonic acid or 4,4'-diamino-diphenyl ether.

EXAMPLE 13

6.37 Parts of 2,6-diaminonaphthalene-4,8-disulphonic acid are dissolved in 100 parts of water with the addition of sodium hydroxide solution at pH 7.3. The solution is cooled to 0° C. by adding ice and a solution of 7.4 parts of cyanuric chloride in 25 parts of acetone is added. Then condensation is carried out at 0° to 5° C. and at pH 6 to 6.5. When no more free amino groups are detectable a neutral solution of 7.5 parts of 1,4-phenylenediamine-2-sulphonic acid in 50 parts of water are added and condensation is carried out at 30° C. and a pH of 6 to 7. Upon completion of the condensation, 10 parts by volume of a 4 normal aqueous sodium nitrite solution are added and the resulting solution is poured on a mixture of 10 parts of 32% hydrochloric acid and 150 parts of ice. The tetrazotisation is terminated after stirring for 1 hour. The suspension of the tetrazonium compound is then treated with a solution of 12.4 parts of the sodium salt of 1-(2'-chlorophenyl)-3-sulphomethyl-pyrazolone-5 in 100 parts of water and coupling is performed at 0° to 5° C., during which the pH of the coupling mixture is kept between 7 and 8. The dyestuff is obtained from the clear reddish yellow solution of the tetrazo dyestuff of the formula

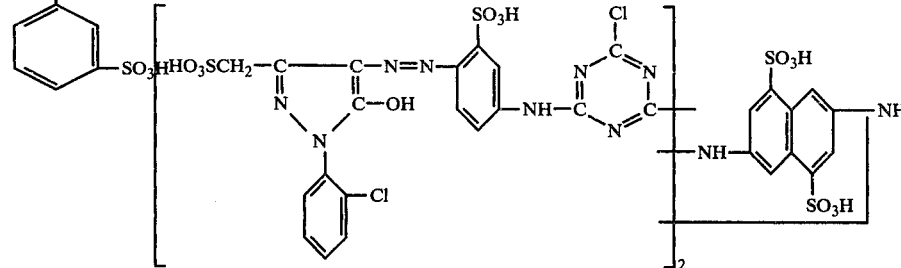

by salting out with common salt. The dyestuff dyes cotton fabric in fast, reddish yellow shades.

EXAMPLE 14

17.3 Parts of 1-aminobenzene-3-sulphonic acid and 18.3 parts of cyanuric chloride are condensed initially as described in Example 1. The monocondensate is reacted with 18.8 parts of 1,3-phenylenediamine-4-sulphonic acid and diazotisation is carried out. The resulting diazo suspension is treated with a solution of 29.1 parts of the sodium salt of 1-(4'-aminophenyl)-3-sulphomethyl-pyrazolone-5. The pH of the coupling mixture is adjusted to 8 by the dropwise addition of sodium hydroxide solution and the mixture is stirred at 0° to 5° C. until the reaction has been brought to completion. Then phosgene is passed through the yellow dyestuff solution at 30° C. to 40° C. until no more free amino groups can be detected. A pH of 7 to 8 is kept during the phosgenation. The dyestuff is precipitated by addition of sodium chloride; it dyes cotton in fast, yellow shades.

EXAMPLE 15

75.3 Parts of the aminopyrazolone dyestuff (obtained in accordance with the directions of Example 14) of the formula

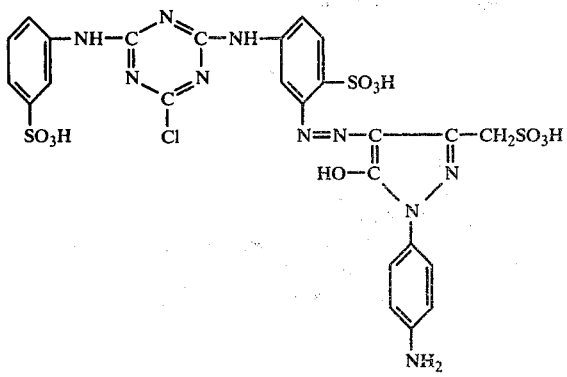

are dissolved in water at pH 7. 16.5 parts of 2-amino-4,6-dichloro-1,3,5-triazine are added and condensation is performed at 30° to 40° C., during the course of which the pH is kept at 6 to 7 by the dropwise addition of 2 normal sodium hydroxide solution. Upon completion of the condensation, the bisreactive dyestuff is precipitated by addition of common salt and dried in vacuo. The dyestuff is obtained in the form of an orange dyestuff powder which dyes cotton in fast, reddish yellow shades.

EXAMPLE 16

41.7 Parts of the reactive dyestuff of the formula

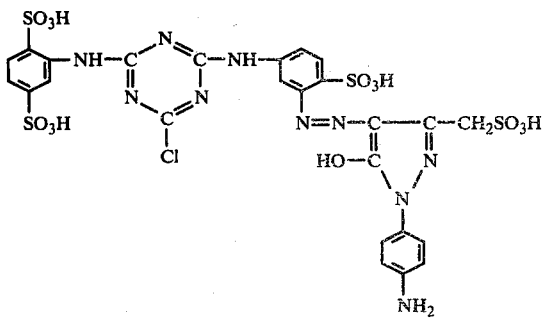

are diazotised in the conventional manner in aqueous hydrochloric acid solution by the dropwise addition of 25 parts by volume of 2 normal sodium nitrite solution. 16.1 parts of 2-(3'-sulphophenylamino)-4,6-dichloro-1,3,5-triazine are condensed with 13.5 parts of 1-(4'-aminophenyl)-3-sulphomethyl-pyrazolone-5. The solution of the diazotised dyestuff is combined with the solution of the coupling component and the pH is adjusted to 6 by addition of sodium bicarbonate. Upon completion of the coupling, the bisreactive disazo dyestuff is precipitated by sprinkling in potassium chloride, filtered off with suction, and dried. It dyes cellulosic fabric in fast, yellow shades.

Manufacturing instructions for 3-sulphomethylpyrazolones

I. 1-phenyl-3-sulphomethylpyrazolone-(5)

To a solution of 30 parts of anhydrous sodium sulphite in 200 parts by volume of water are added at 50° C. 33 parts of γ-chloroacetoacetic ester and the mixture is stirred at the indicated temperature until all is dissolved. Then 21.2 parts of phenylhydrazine are added and stirring is continued for 1 hour at 80° to 85° C. The batch is cooled to room temperature, then made strongly acid to Congo red with 40 parts by volume of concentrated hydrochloric acid. The precipitated product is filtered with suction and dried.

II. 3-sulphomethylpyrazolone-(5)

164.5 parts of γ-chloroacetoacetic ester are rapidly passed into a solution of 150 parts of sodium sulphite in 100 parts of water. The exothermic reaction causes the temperature to rise to 60° C. and a clear solution forms. Then 53 parts of hydrazine hydrate are added all at once and the batch is made strongly alkaline with 150 parts by volume of 30% sodium hydroxide solution and heated for 1 hour to 90° C. After the solution has cooled, the pH is adjusted to 5 by the dropwise addition of hydrochloric acid. The resulting solution of 3-sulphomethylpyrazolone, whose content can be determined by titration with 4-nitrobenzene-diazonium chloride solution, can be used direct for the manufacture of azo dyestuffs. The corresponding pyrazolones which are substituted in 3-position of the pyrazolone ring by a sulphomethyl group are also obtained by substituting equivalent amount of methyl hydrazine, ethyl hydrazine, 2-chloro-phenyl hydrazine, 2-methylphenyl hydrazine, phenyl hydrazine-2,3-sulphonic acid or phenyl hydrazine-4-sulphonic acid for hydrazine hydrate.

Dyeing Instruction I 2 parts of the dyestuff of Example 1, 1st. paragraph, are dissolved in 100 parts of water. A cotton fabric is impregnated on a padder with this solution and the excess liquid is squeezed out so that the material retains 75% of its weight of dyestuff solution.

The article so impregnated is dried, then impregnated at room temperature with a solution which contains, per liter, 10 g of sodium hydroxide and 300 g of sodium chloride, squeezed out to 75% liquid pick-up, and steamed at 100° C. to 101° C. for 60 seconds. The article is then rinsed, soaped at the boil for a quarter of an hour in a 0.3% solution of an ion-free detergent, rinsed, and dried.

A fixed dyeing which is fast to boiling is obtained. A similarly good result is obtained by using a cellulose fabric instead of a cotton one.

Dyeing Instruction II 4 parts of the chromium dyestuff obtained according to Example 7 are dissolved in 4000 parts of water and 100 parts of well moistened wool flannel are put into this dyebath at 40° C. to 50° C. The 3 parts of 40% acetic acid are added to the bath which is heated within ½ hour to the boil and kept at boiling point for ¾ hour. The dyed goods are rinsed with cold water and dried. The resulting red dyeing has very good fastness to light and wet treatment. Wool dyeings with similarly good fastness properties are obtained by using a dyebath which contains formic instead of acetic acid.

Printing Instruction 2 parts of the dyestuff obtained according to Example 2 are mixed with 20 parts of urea, dissolved in 28 parts of water, and stirred into 40 parts of a 5% strength sodium alginate thickener. 10 parts of a 10% strength sodium carbonate solution are then added.

A cotton fabric is printed on a roller printing machine using this printing ink, is dried, and the print obtained is steamed at 105° C. for 8 minutes. The printed fabric is then thoroughly rinsed in cold and hot water and dried.

We claim:

1. An azo dyestuff of the formula

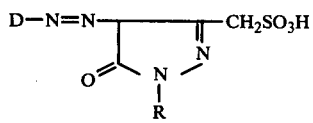

wherein
D is phenyl or phenyl substituted by chloro, bromo, methyl, nitro, cyano, trifluoromethyl, carbomethoxy, carboethoxy, cyclohexylcarbonyloxy, N-methylsulfonamido, N,N-dimethylsulfonamido, N,N-diethylsulfonamido, N,γ-isopropyloxypropylsulfonamido, N-isopropylsulfonamido, N,γ-methoxypropylsulfonamido, N,N-bis(β-hydroxyethyl)sulfonamido, sulfonamido, phenylazo, methoxyphenylazo, tolylazo, chlorophenylazo, dichlorophenylazo, sulfonamidophenylazo, acetylamino, hydroxy, acetyl, carboxamido, methylsulfonyl, sulfo, N-(β-hydroxyethyl)sulfonamido, ethylsulfonyl, β-hydroxyethylsulfonyl, carboxy, benzoylamino, disulfophenylazo, disulfonapthylazo, sulfophenylazo, (carboxy, sulfo) phenylazo, β-sulfatoethylsulfonyl, β-sulfoethylsulfonylmethylamido, or a fiber reactive group containing a halo substituted six-membered heterocyclic radical with two or three ring nitrogen atoms and capable of reacting with the hydroxyl groups of cellulose or the amino groups of polyamides to form a covalent bond therewith, and bonded via an —NH— group; napthyl or napthyl substituted by N,γ-isopropyloxypropylsulfonamido, carboxy, hydroxy, sulfo, sulfonamido, nitro, acetylamino, disulfophenylazo, methoxy, or said fiber-reactive group containing a six-membered heterocyclic radical bonded via an —NH— group; thiazolyl-(2) which is unsubstituted or substituted by methylsulfonyl methyl, phenyl, or 4-chlorophenyl; benzisothiazolyl-(3) which is unsubstituted or substituted by chloro; pyridinyl-(3); quinolinyl-(3) or -(2); pyrazolyl-(3) which is unsubstituted or substituted by phenyl or 4-methoxyphenyl; indazolyl-(3); benzthiazolyl-(2) which is unsubstituted or substituted by methyl, methoxy or chloro; 1,2,4-triazolyl-(3) which is unsubstituted or substituted by methyl, ethyl, phenyl or benzyl; 1,3,4-thiadiazolyl-(2); or 1,3,5-thiadiazolyl-(2) which is unsubstituted or substituted by phenyl or methyl; and
R is hydrogen; alkyl of 1 to 4 carbon atoms; hydroxyethyl; cyanoethyl; methoxyethyl; cyclohexyl; benzyl; disulfonaphthyl; or phenyl which is unsubstituted or substituted by methyl, methoxy, chloro, bromo, fluoro, nitro, sulfo, $NH_2$—, acetylamino or a group of the formula

wherein
R' is hydrogen, alkyl of 1 to 4 carbon atoms or hydroxyethyl, and
Z is said fiber reactive group containing a six-membered heterocyclic radical.

2. An azo dyestuff according to claim 1 of the formula

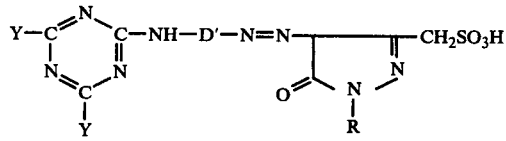

wherein
D' is mono- or di-sulfophenylene,
one Y is chloro or bromo and the other Y is chloro; bromo; $NH_2$—; phenylamino or phenylamino substituted by sulfo, carboxy, sulfomethyl, β-chloroethylsulfonyl, chloroacetylaminomethyl; sulfonapthylamino; N-phenyl, N-sulfomethyl amino; methoxy; ethoxyethoxy; 6-chloro-4-amino-1,3,5-triazine-2-yl-amino-sulfophenylamino; 6-chloro-4-sulfophenylamino-1,3,5-triazine-2-ylaminophenylamino; 6-chloro-4-sulfophenylamino-1,3,5-triazine-2-ylamino-sulfophenylamino; methylmercapto; isopropoxy; ethylamino; morpholino; ureido; or dimethylaminosulfonylamino.

3. An azo dyestuff according to claim 1 of the formula

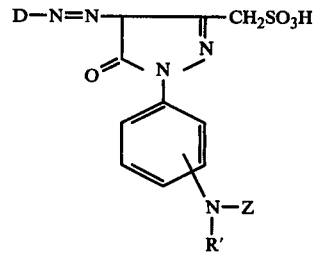

wherein
D is said phenyl, napthyl or substituted phenyl or napthyl.

* * * * *